(12) United States Patent
Bonanomi et al.

(10) Patent No.: US 9,828,380 B2
(45) Date of Patent: Nov. 28, 2017

(54) EFFICIENT METHOD FOR THE PREPARATION OF TOFACITINIB CITRATE

(71) Applicant: OLON S.p.A., Rodano (IT)

(72) Inventors: Jacopo Bonanomi, Rodano (IT); Stella Defiore, Rodano (IT); Barbara Novo, Rodano (IT)

(73) Assignee: OLON S.P.A., Rodano (IT)

( * ) Notice: Subject to any disclaimer, the term of this patent is extended or adjusted under 35 U.S.C. 154(b) by 0 days.

(21) Appl. No.: 15/092,651

(22) Filed: Apr. 7, 2016

(65) Prior Publication Data

US 2016/0297825 A1 Oct. 13, 2016

(30) Foreign Application Priority Data

Apr. 10, 2015 (IT) .................. 102015000011506

(51) Int. Cl.
*C07D 487/00* (2006.01)
*C07D 487/04* (2006.01)
(Continued)

(52) U.S. Cl.
CPC .......... *C07D 487/04* (2013.01); *C07C 51/412* (2013.01); *C07C 69/76* (2013.01);
(Continued)

(58) Field of Classification Search
None
See application file for complete search history.

(56) References Cited

FOREIGN PATENT DOCUMENTS

| CN | 104341422 A | 2/2015 |
|----|-------------|--------|
| WO | WO02/096909 | * 12/2002 |

(Continued)

OTHER PUBLICATIONS

Marican Adolfo, et al., "Asymmetric total synthesis of Tofacitinib", Tetrahedron Letters, vol. 54, No. 37, Jul. 13, 2013, pp. 5096-5068.
(Continued)

*Primary Examiner* — Jeffrey H Murray
(74) *Attorney, Agent, or Firm* — Silvia Salvadori, P.C.; Silvia Salvadori

(57) ABSTRACT

Disclosed is a novel process for the synthesis of tofacitinib citrate on an industrial scale with high yields and purity starting with cis-(1-benzyl-4-methyl-piperidin-3-yl)methyl-amine bis-hydrochloride racemate (intermediate VIII), which comprises:

1. Condensation between intermediates VII and VIII to give intermediate VI
2. Hydrogenation of intermediate VI to give intermediate V
3. Resolution of intermediate V to give intermediate IV with enantiomeric purity >99%
4. Release of intermediate IV in a basic medium to give intermediate III
5. N-acylation reaction of intermediate III to give II (tofacitinib)
6. Salification of intermediate II to give tofacitinib monocitrate (I)

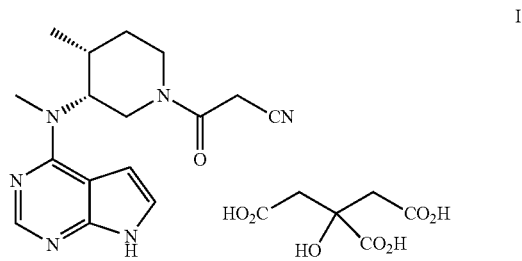

I

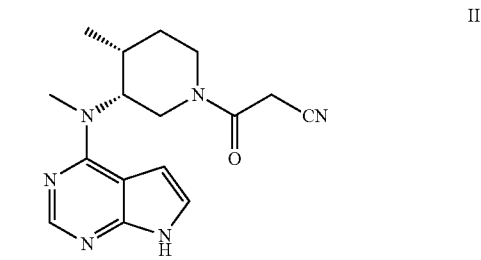

II

III

IV (Continued)

-continued

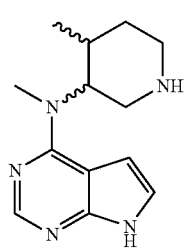

V

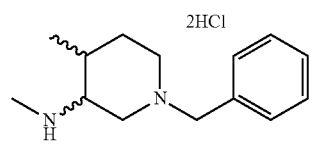

VIII

R = H, methyl

9 Claims, 12 Drawing Sheets

(51) Int. Cl.
  *C07C 69/76* (2006.01)
  *C07C 69/78* (2006.01)
  *C07C 51/41* (2006.01)

(52) U.S. Cl.
  CPC .......... *C07C 69/78* (2013.01); *C07B 2200/07* (2013.01); *C07B 2200/13* (2013.01)

(56) References Cited

FOREIGN PATENT DOCUMENTS

| WO | 2007012953 | A2 | 2/2007 |
| WO | 2010014930 | A2 | 2/2010 |
| WO | 2010123919 | A2 | 10/2010 |
| WO | 2014195978 | A2 | 12/2014 |

OTHER PUBLICATIONS

Patil Yogesh, S., et al., "An improved and efficient process for the preparation of tofacitinib citrate," Organic Process Research & Development, vol. 18, No. 12, Dec. 19, 2014, pp. 1714-1720.
Search Report and Written Opinion of Italian Patent Application No. 102015000011506 dated Aug. 6, 2015.

\* cited by examiner

VI

VII

EFFICIENT METHOD FOR THE PREPARATION OF TOFACITINIB CITRATE

This Application claims priority to and the benefit of Italian Patent Application No. 102015000011506 filed on Apr. 10, 2015 incorporated herein by reference it its entirety.

FIELD OF INVENTION

The present invention relates to a novel process for the synthesis of high-purity tofacitinib citrate.

BACKGROUND TO THE INVENTION

Pyrrolo[2,3-d] pyrimidine compounds are potent inhibitors of protein kinase, such as the enzyme Janus Kinase 3 (JAK 3), and are therefore useful in the treatment of a wide range of autoimmune disorders such as lupus, multiple sclerosis, rheumatoid arthritis, psoriasis, type 1 diabetes and the complications thereof, cancer, asthma, atopic dermatitis, autoimmune thyroid disorders, ulcerating colitis, Crohn's disease, Alzheimer's disease and leukaemia. Said compounds are also useful in the treatment and prevention of rejection following organ transplant.

Tofacitinib citrate (I) (FIG. 1) is an active ingredient belonging to the class of Janus Kinase inhibitors. It is currently used in the treatment of rheumatoid arthritis, and under study for the treatment of psoriasis and other autoimmune disorders.

The preparation of tofacitinib (II) and the monocitrate salt I thereof was disclosed for the first time in WO2001/042246, wherein intermediate VI is obtained with the method of direct condensation between VII and VIII. Through hydrogenation of VI, the amino position of the piperidine residue is deprotected to obtain intermediate V, which can then be N-acylated with cyanoacetic acid or derivatives thereof to give firstly tofacitinib free base (intermediate II), and finally I after salification with citric acid. The structures of said intermediates are reported in FIG. 1.

Said document does not give any indications about the stereochemistry of the intermediates or the product. The process presented in WO2001/042246 involves a number of drawbacks, especially the fact that product I is obtained with a total molar yield of 6%. Moreover, for the first step, namely condensation between VII and VIII to give intermediate VI, the operational procedure involved is difficult to implement on an industrial scale; condensation is performed using triethylamine as solvent, and a pressure sufficient to enable the mixture to reach 100° C. is applied; the product is only obtained after a 3-day reaction, and isolation by silica-gel column chromatography.

Purification by silica-gel column chromatography is also required to isolate the next intermediate (intermediate V).

WO0209/6909 describes the same synthesis route, albeit with some procedural variations, but with precise references to the stereochemistry of the intermediates involved (Scheme 1).

Here, intermediate VIII is first resolved to give optically active IX, and only at this point is it condensed with intermediate VII to give X, which is also optically active; this process produces tofacitinib citrate (I) with high enantiomeric purity.

However, said process has some critical factors, especially the fact that one of the two methods proposed for resolution of VIII involves the use of an expensive resolving agent (phencyphos). Moreover, in the condensation between VII and IX, intermediate X is obtained in a low yield (54%), and purification by silica gel column chromatography is required to isolate the next intermediate (intermediate III).

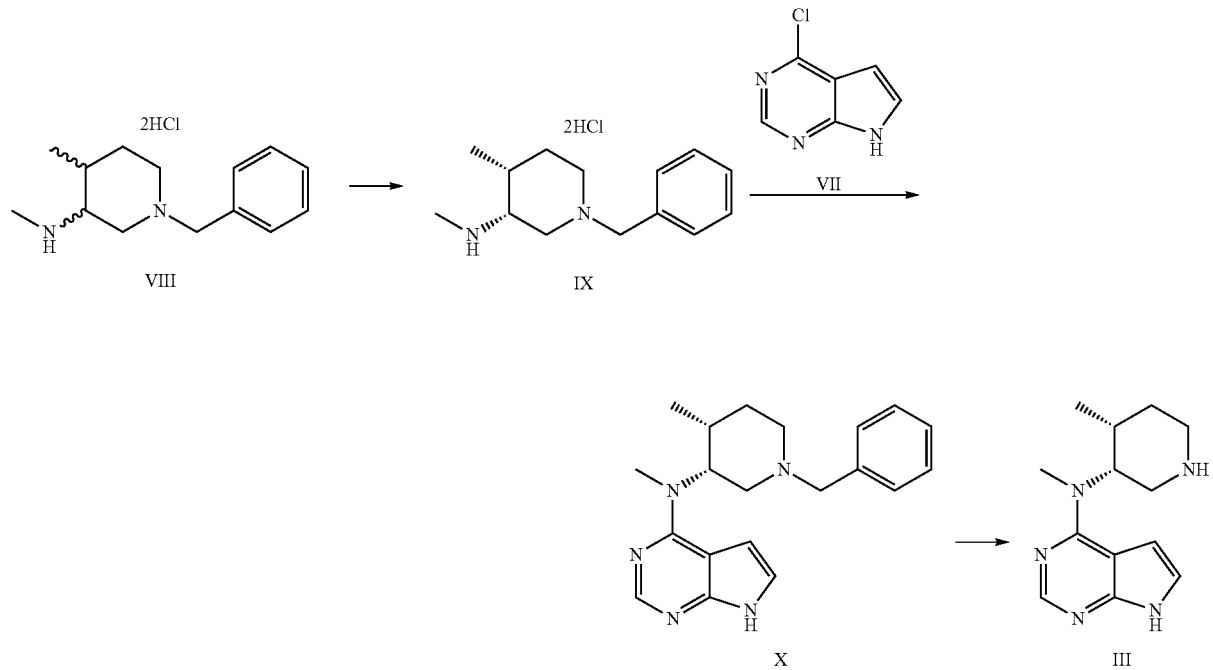

Scheme 1

-continued

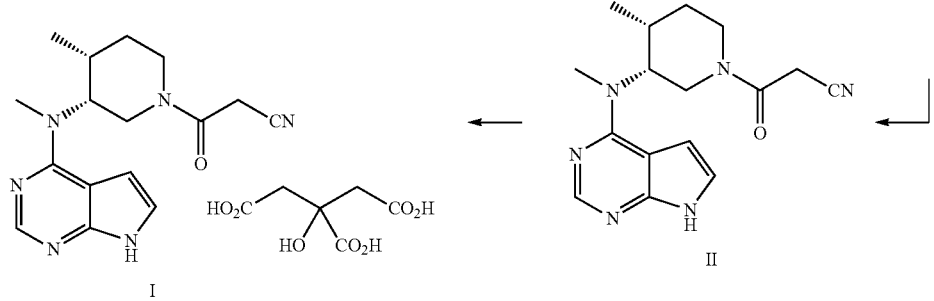

WO2007/012953 discloses two alternative synthesis processes wherein intermediate VII is activated in one case by the presence of a tosyl group and in the other by a chlorine atom.

The first process (Scheme 2) can be summarised as follows:
1. Activation of VII to give intermediate XI
2. Resolution of VIII to give IX
3. Condensation between intermediate XI and intermediate IX to give intermediate XII
4. Removal of activating group from XII to give intermediate X
5. Hydrogenation of intermediate X to give intermediate III 6. N-acylation reaction of intermediate III to piperidine nitrogen to give intermediate II (tofacitinib)
7. Salification of intermediate II to give tofacitinib monocitrate (I)

Although this process provides a significant increase in global molar yield (18-20 percentage points), it involves two more synthesis steps than the process illustrated in WO02/096909. Moreover, document WO2007/012953 describes an alternative method of obtaining compound IX with high enantiomeric purity which, although it is innovative compared with the resolution of VIII to give IX already described in WO02/096909, is particularly onerous, especially if applied on a large scale, because it involves the use of an expensive rhodium-based catalyst during the asymmetrical reduction of the pyridine ring of VIII to give IX.

Scheme 2

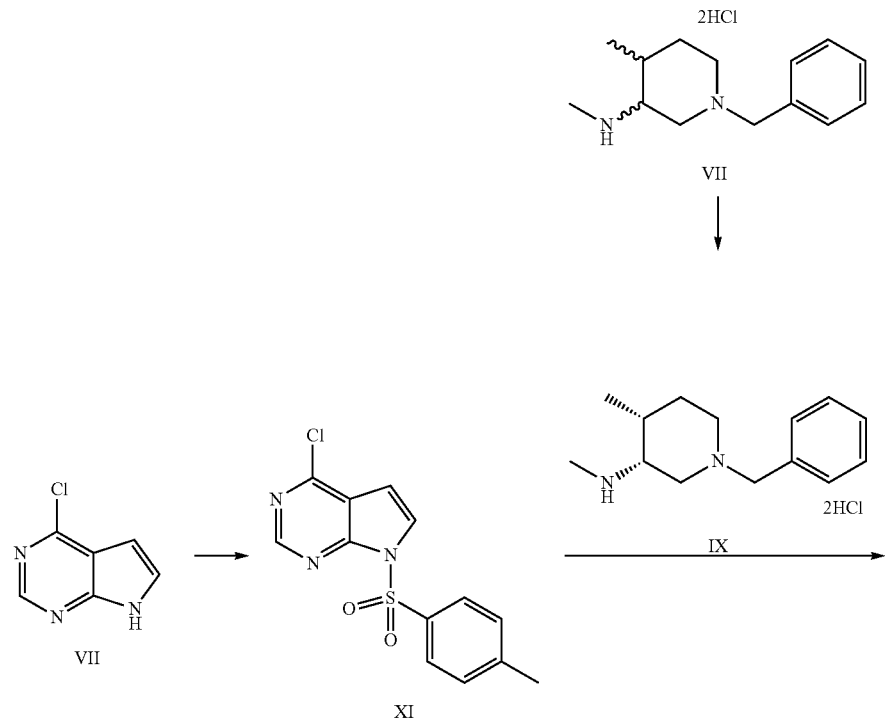

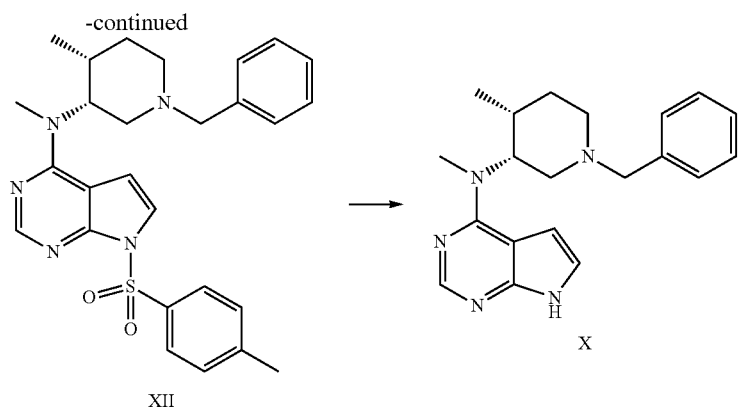

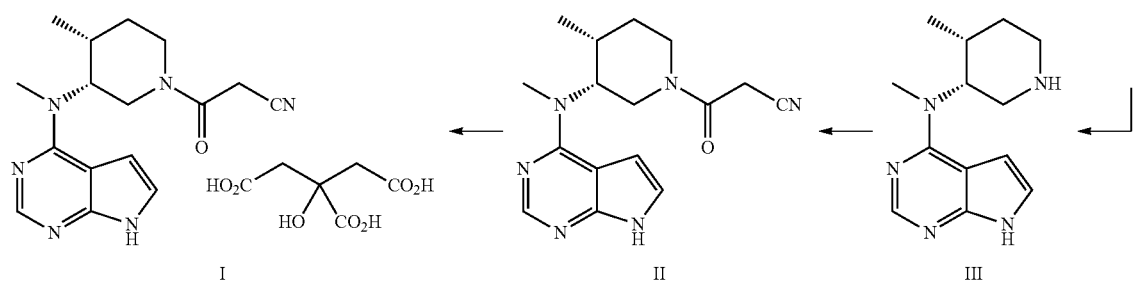

The second process (Scheme 3) can be summarised as follows:
1. Resolution of VIII to give IX
2. Condensation between intermediate XIII and intermediate IX to give intermediate XIV
3. Hydrogenation of intermediate XIV to give intermediate III
4. N-acylation reaction of intermediate III to give intermediate II
5. Salification of intermediate II to give tofacitinib monocitrate (I)

Scheme 3

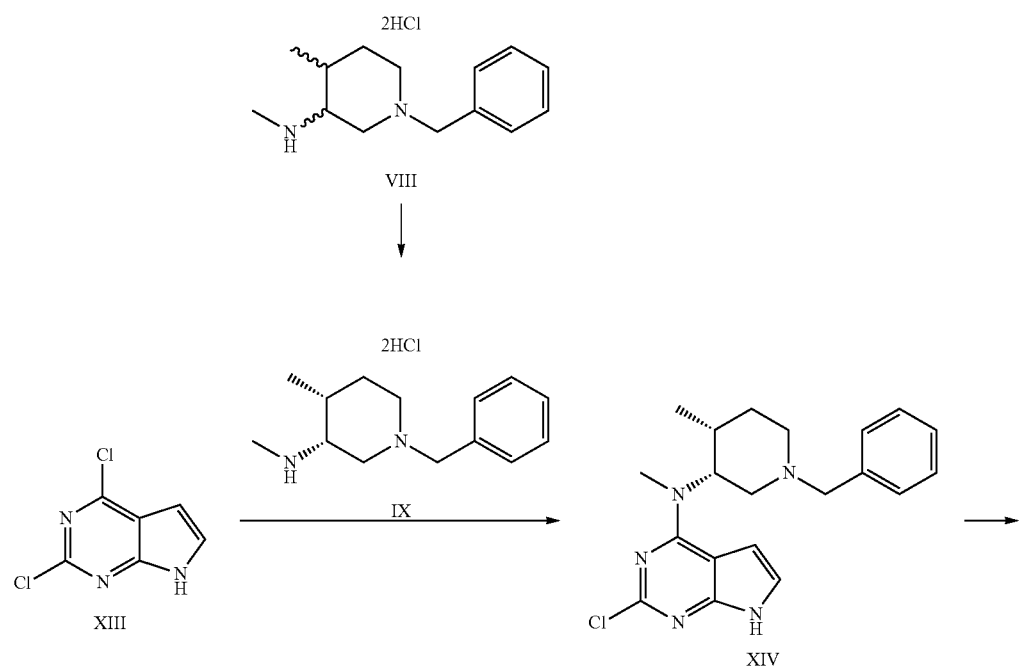

-continued

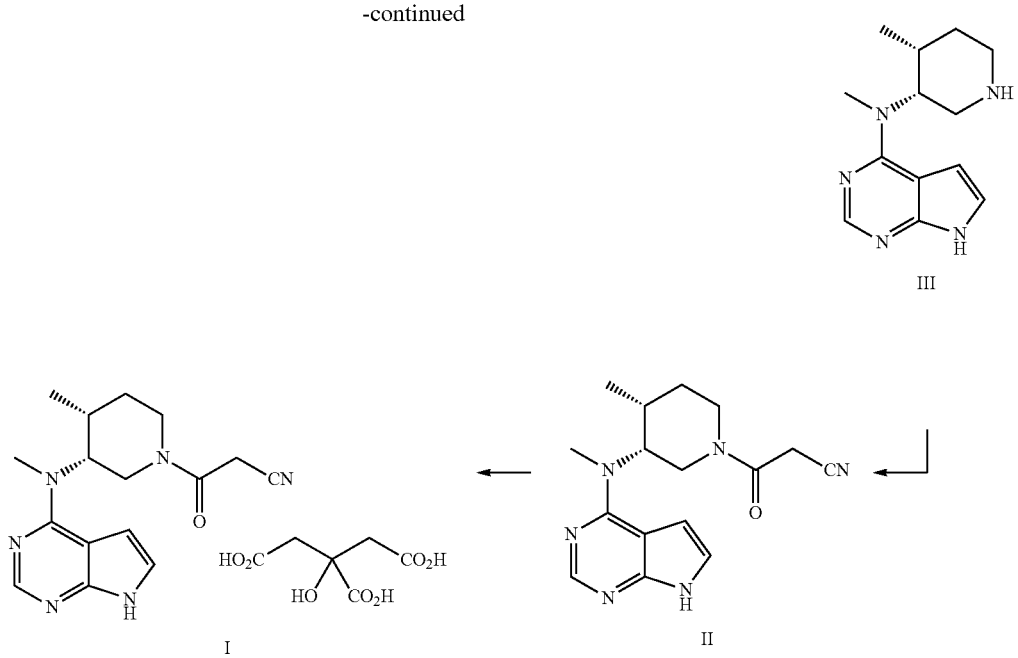

In this process the number of steps is limited and the global molar yield is high; however, the main drawback thereof is represented by the use of a raw material (compound XIII) which is much more expensive than the one used in the other processes (compound VII).

There is consequently still a need to find a synthesis route which is industrially scalable and gives tofacitinib with higher yields and purity.

The present patent application therefore illustrates an alternative method of obtaining intermediate III with no need to resolve VIII.

DESCRIPTION OF THE INVENTION

Figure 1:
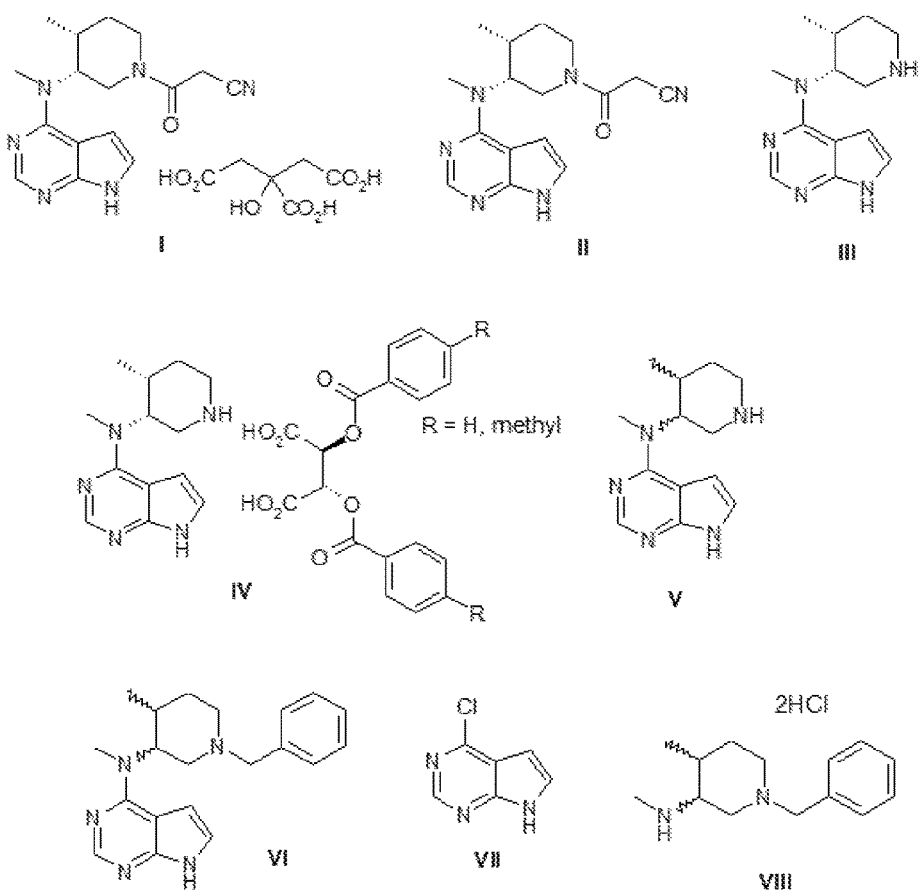
FIG. 1: Structures of tofacitinib citrate (I) and the main intermediates of the process according to the invention

We have surprisingly found that tofacitinib and the pharmaceutically acceptable salts thereof, in particular tofacitinib monocitrate, can be obtained with high purity and high yields by an efficient, innovative process by using intermediates not resolved up to the level of intermediate V. On the basis of the literature cited above, it was not foreseeable that excellent purity, an excellent enantiomeric excess, and simultaneously crystalline intermediates could be obtained with high yields, thus eliminating the need for chromatography.

Said process also presents numerous advantages, including a limited number of synthesis steps, isolation of products not requiring purification by silica-gel column chromatography, a high global molar yield and the use of raw materials and reagents which are readily commercially available and inexpensive.

The process according to the invention (Scheme 4) can be summarised as follows:

1. Condensation between intermediates VII and VIII to give intermediate VI
2. Hydrogenation of intermediate VI to give intermediate V
3. Resolution of intermediate V with 2,3-dibenzoyl-D-tartaric acid or 2,3-di-(p-toluoyl)-D-tartaric acid to give intermediate IV, wherein R is hydrogen or methyl, with enantiomeric purity exceeding 99%
4. Treatment of intermediate IV with bases to give intermediate III
5. N-acylation reaction of intermediate III to give intermediate II (tofacitinib)
6. Optional salification of intermediate II to give tofacitinib monocitrate (I)

Scheme 4

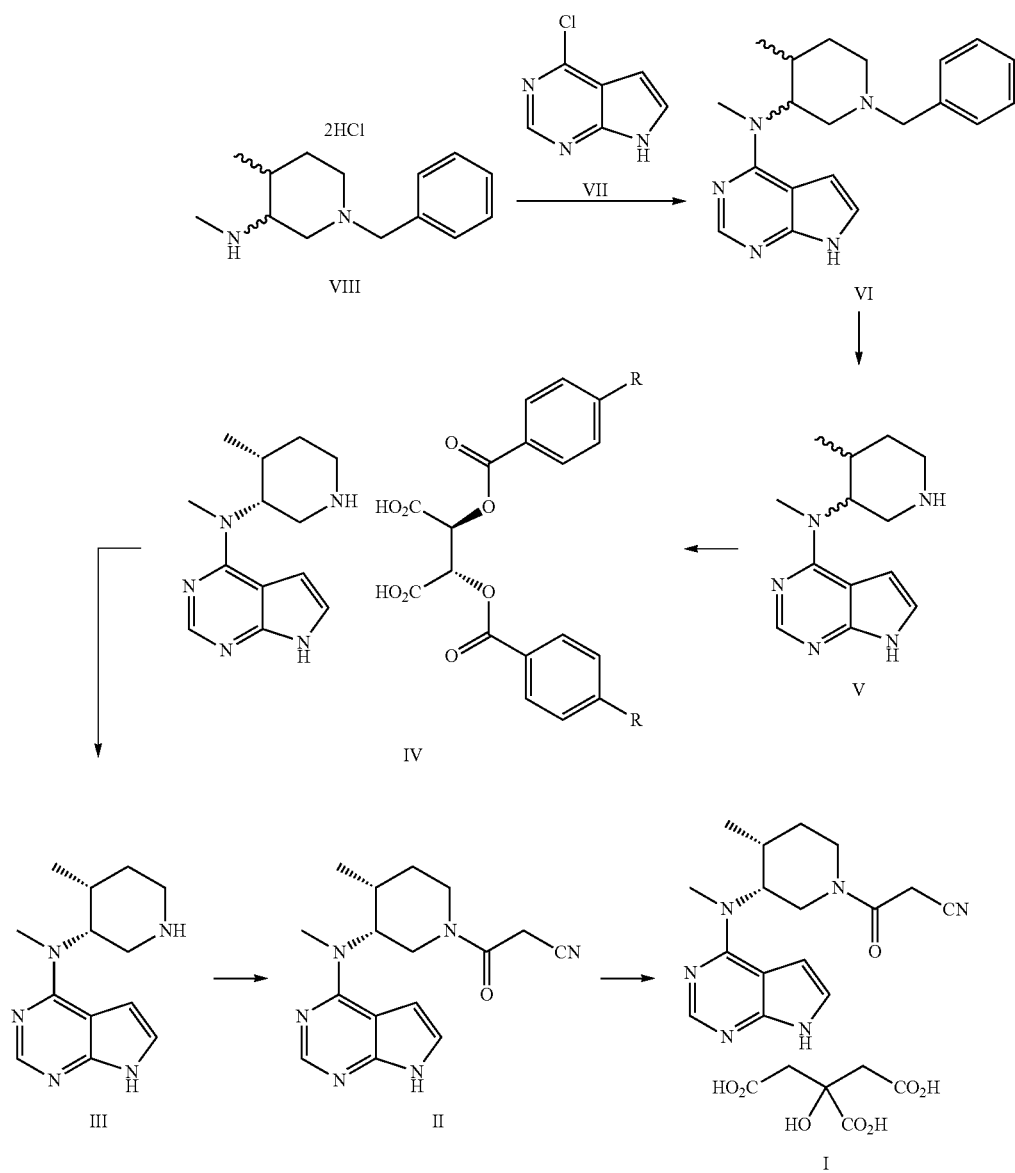

R = H, methyl

DETAILED DESCRIPTION OF THE INVENTION

Both starting substrates of the synthesis process claimed, namely 4-chloro-7H-pyrrolo[2,3-d]pyrimidine (VII) and (3,4)-N,4-dimethyl-1-(phenylmethyl)-3-piperidinamine bis-hydrochloride (VIII), are commercially available.

Step 1: Condensation of 4-chloro-7H-pyrrolo[2,3-d]pyrimidine(VII) and N,4-dimethyl-1-(phenylmethyl)-3-piperidinamine bis-hydrochloride(VIII)

The condensation reaction is carried out in polar solvent in the presence of a hydrogen acceptor. The condensation is effected at reflux temperature.

The reaction can be conducted using dioxane, n-butanol, water or isopropanol as solvent, preferably water.

The hydrogen acceptor can be selected from organic or inorganic bases, preferably inorganic. Of the inorganic bases, sodium carbonate or potassium carbonate is preferably used.

The reaction is carried out with a stoichiometric ratio of intermediate VII to intermediate VIII ranging between 1 and 2, preferably between 1.1 and 1.5, more preferably between 1.1 and 1.2.

The reaction time is between 36 and 72 hours, preferably between 48 and 60 hours.

To isolate intermediate VI, the reaction mixture is left to cool to below boiling point, a precipitate being obtained after suitable addition of a co-solvent such as acetone, methanol or isopropanol, preferably methanol.

The crude product obtained can be recrystallised from a suitable alcohol- or water/alcohol-based solvent such as methanol, ethanol or isopropanol, preferably isopropanol and ethanol, and even more preferably a mixture consisting of ethanol and water.

Step 2: Hydrogenation of Intermediate VI

V is prepared by metal-catalysed hydrogenation in an acid medium, wherein various operating conditions known from the literature can be used.

Pd/C, Pt/C, Pd(OH)$_2$/ C or other similar catalysts can be used.

The reaction can be conducted using methanol, ethanol, water or isopropanol as solvent, preferably isopropanol and water.

The product is isolated by extraction with organic solvent after removing the catalyst and restoring the pH to alkaline conditions with a suitable base.

Step 3: Resolution of Intermediate V to Give Intermediate IV having an Enantiomeric Purity >99%

Intermediate V can form a wide variety of salts with numerous organic and inorganic acids.

Intermediate IV is prepared with enantiomeric purity exceeding 99% by treatment with a suitable resolving agent, in particular one belonging to the series of benzoyl-functionalised acids of D-tartaric acid, such as 2,3-di-p-toluoyl D-tartaric acid and 2,3-dibenzoyl D-tartaric acid.

The use of functionalised derivatives of tartaric acid belonging to series D promotes the selective precipitation of intermediate IV with the 3R,4R configuration, which is a further object of the invention.

The use of functionalised derivatives of tartaric acid belonging to series L promotes the selective precipitation of intermediate IV with the 3S,4S configuration, which also represents a further object of the invention.

The resolving agent can be anhydrous, hydrated, solvated or co-solvated.

The resolving agent can be used in a stoichiometric ratio ranging between 1 and 5 molar equivalents per molar equivalent of V, preferably in a stoichiometric ratio ranging between 1 and 2 molar equivalents per molar equivalent of V, more preferably in a stoichiometric ratio ranging between 1 and 1.2 molar equivalents per molar equivalent of V.

The amount of solvent to be used ranges between 5 and 20 volumetric equivalents compared with the amount of V, preferably between 8 and 15 volumetric equivalents compared with the amount of V.

Product IV deriving from the resolution process possesses enantiomeric purity exceeding 99%.

Figure 2:
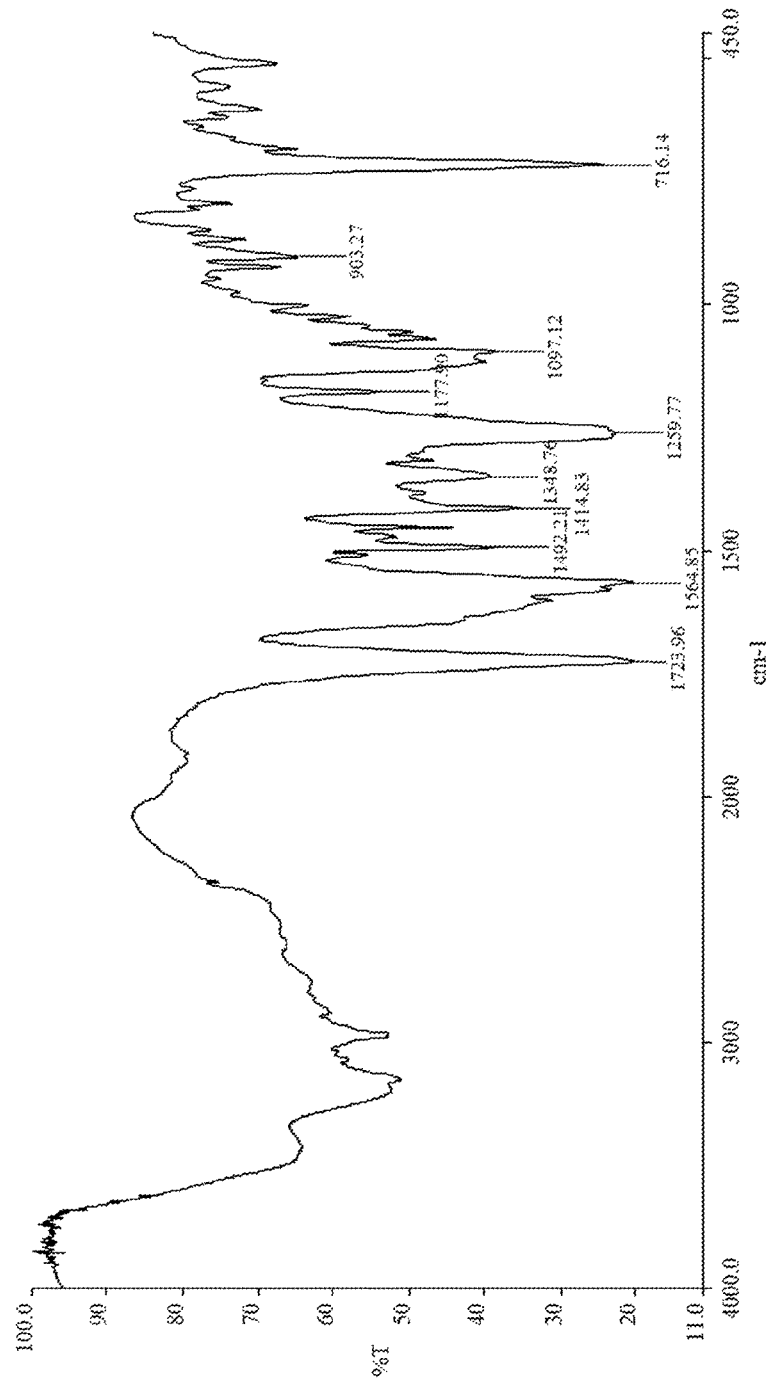
FIG. 2: Infrared spectrum of the crystalline form of the compound of formula IV wherein R is hydrogen.
Figure 3:
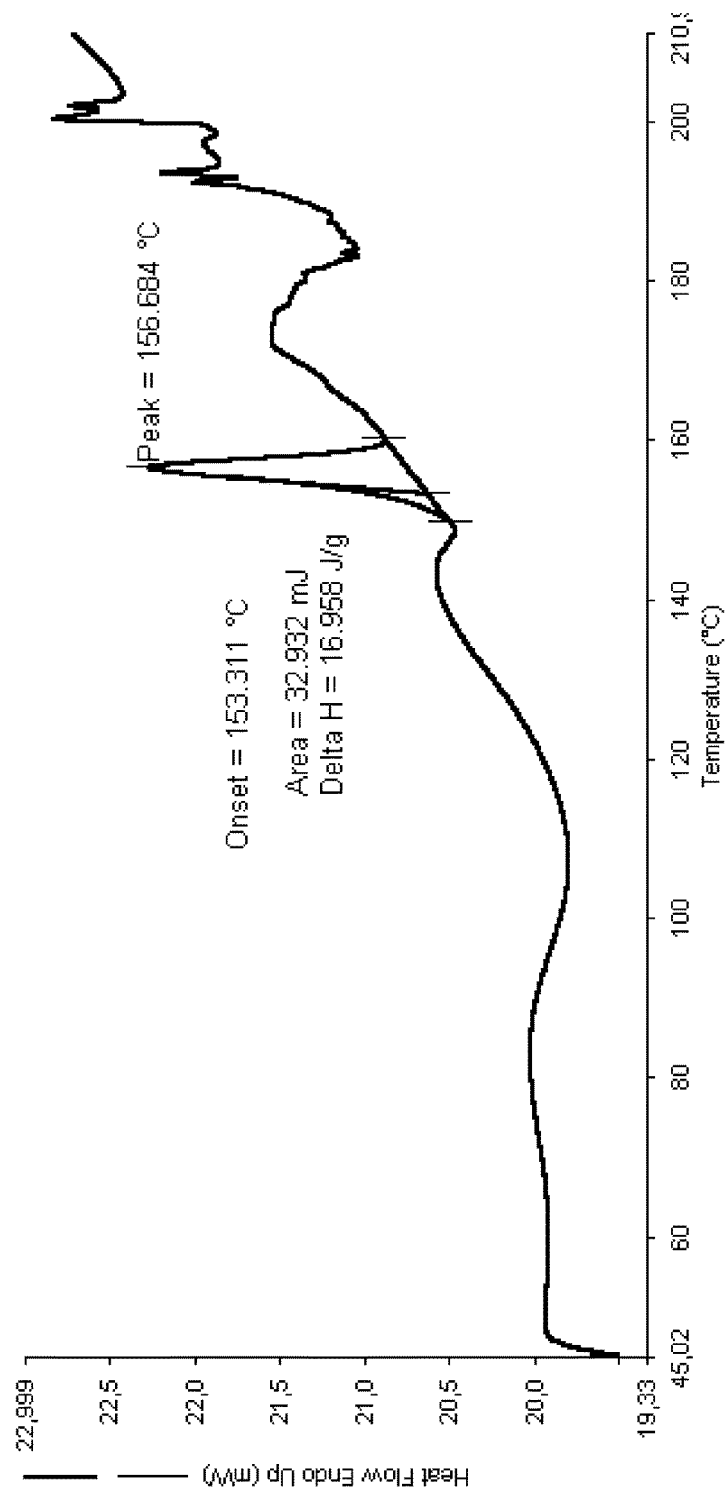
FIG. 3: DSC pattern of the crystalline form of the compound of formula IV wherein R is hydrogen.
Figure 4:
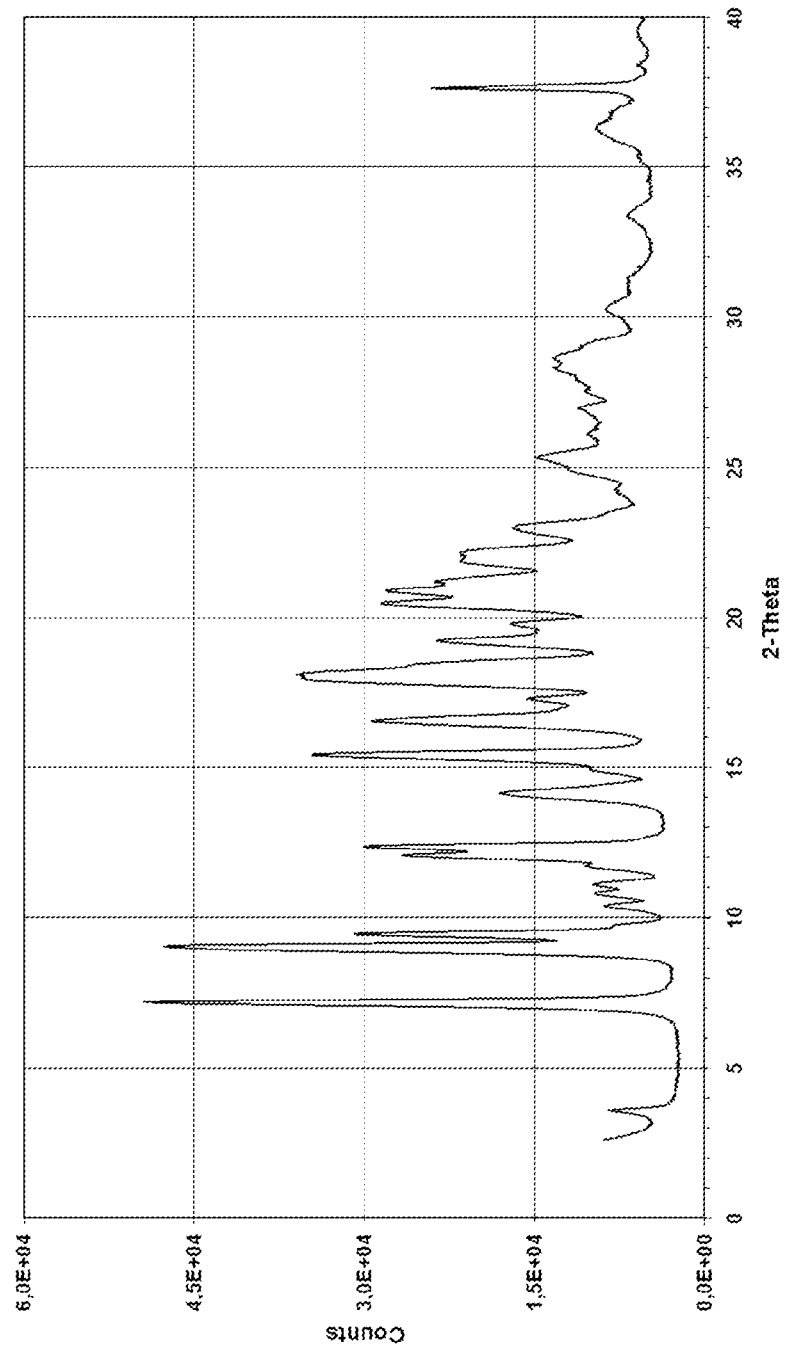
FIG. 4: XRPD pattern of the crystalline form of the compound of formula IV wherein R is hydrogen.
Figure 5:
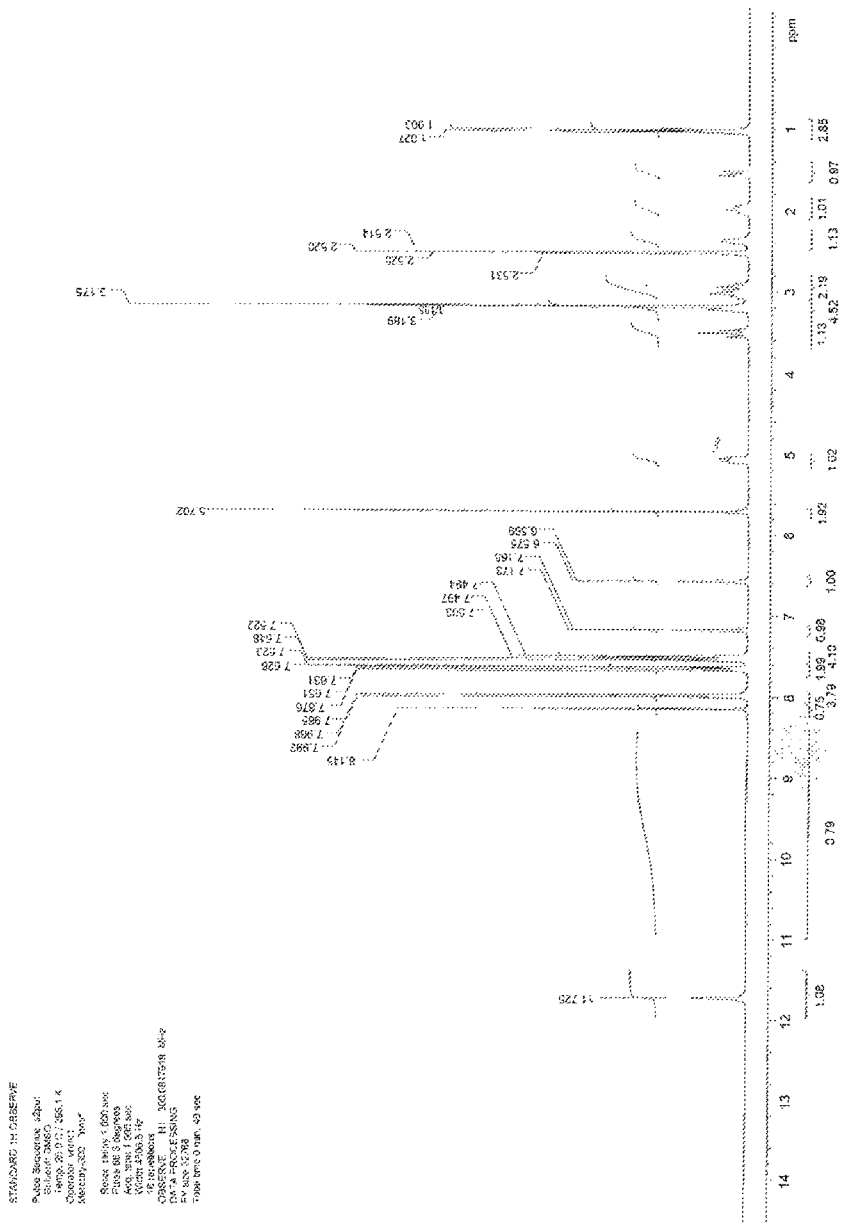
FIG. 5: 1H-NMR spectrum of the crystalline form of the compound of formula IV wherein R is hydrogen.

Intermediate IV, wherein R═H and which has the 3R,4R configuration, exists in a crystalline form obtainable by crystallisation from methanol and having an IR spectrum, DSC pattern and XRPD diffractogram as shown in FIGS. 2, 3 and 4 respectively.

In particular, said crystalline form of intermediate IV presents:
 an IR spectrum comprising absorption peaks at 1723, 1564, 1492, 1414, 1348, 1259, 1177, 1097, 903 and 716±1.5 cm$^{-1}$;
 a DSC pattern comprising an endothermic peak at 156.7° C.;
 an XRPD diffractogram comprising peaks with the following 2θ angle values and intensities: 7.18 (100); 9.03 (96.4); 9.45 (62.5); 12.35 (61); 15.44 (70.1); 16.57 (58.5); 18.09 (72.6); 20.91 (56.7).

Figure 6:
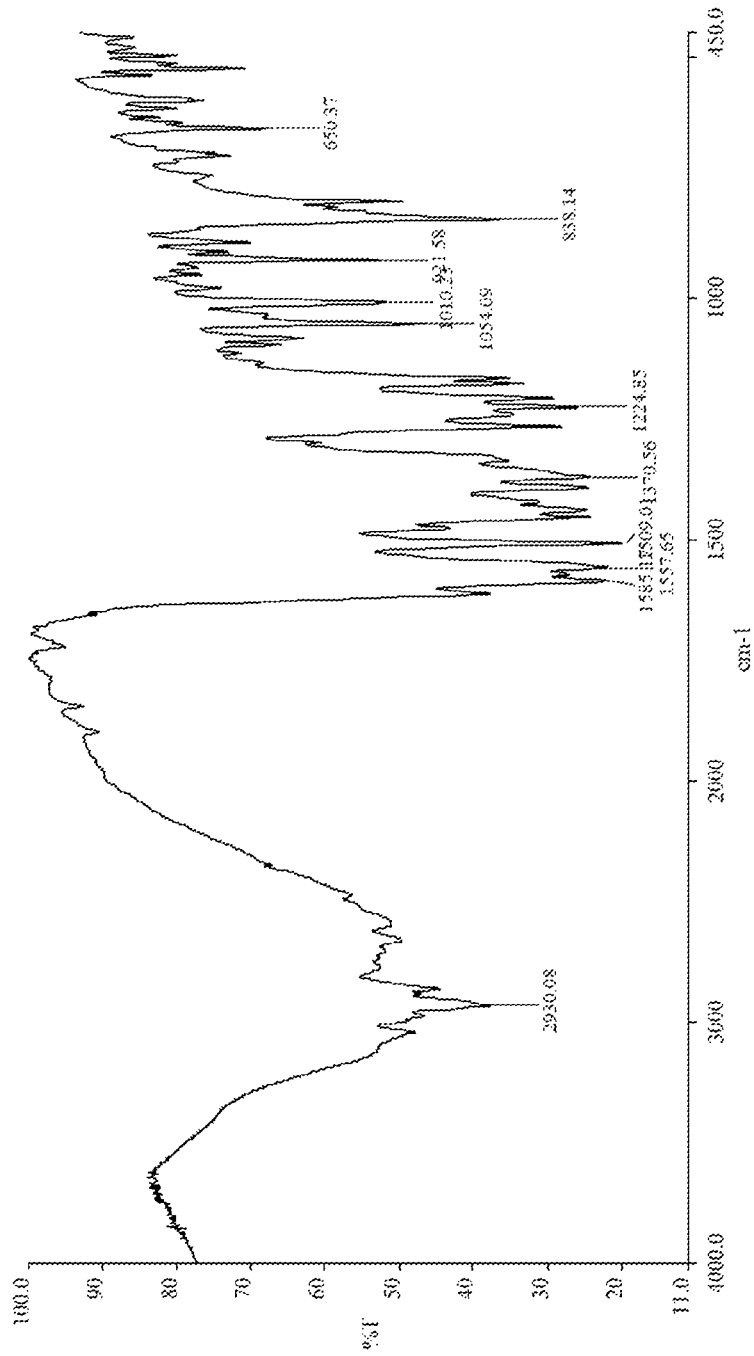
FIG. 6: Infrared spectrum of the amorphous form of the compound of formula IV wherein R is hydrogen.
Figure 7:
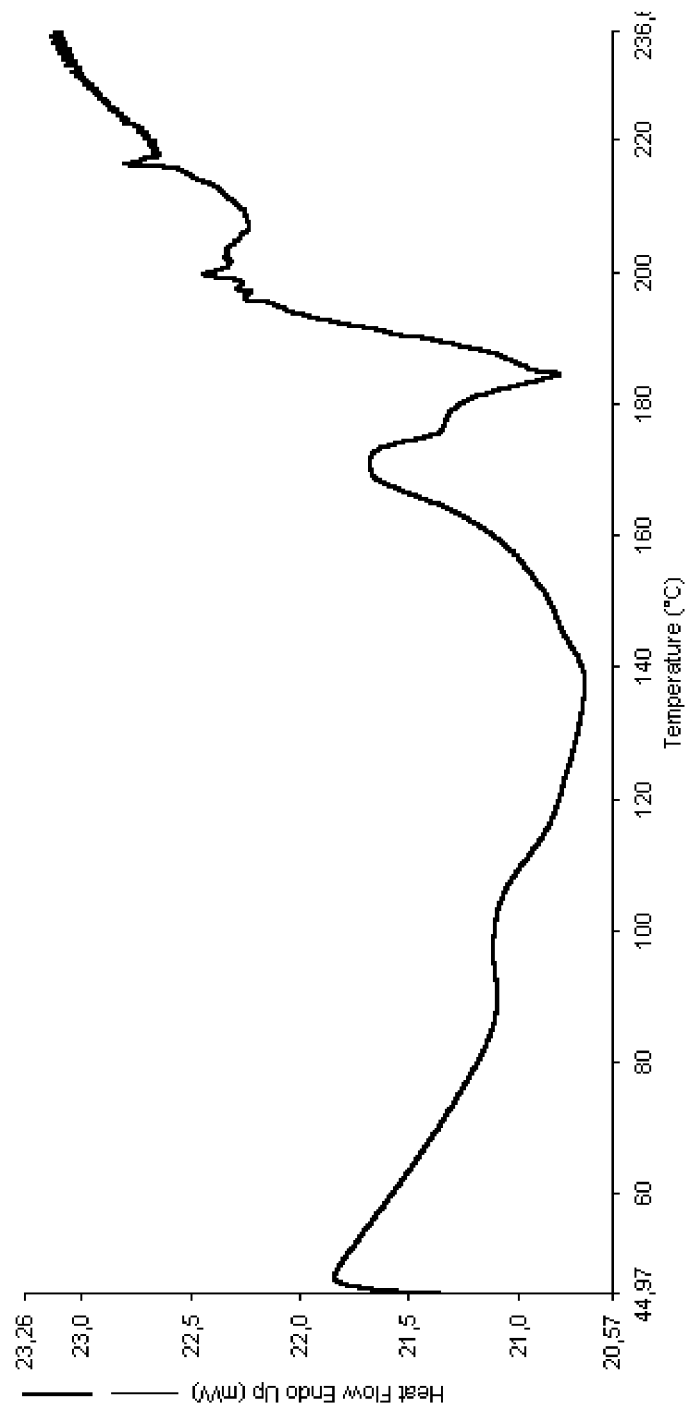
FIG. 7: DSC pattern of the amorphous form of the compound of formula IV wherein R is hydrogen.
Figure 8:
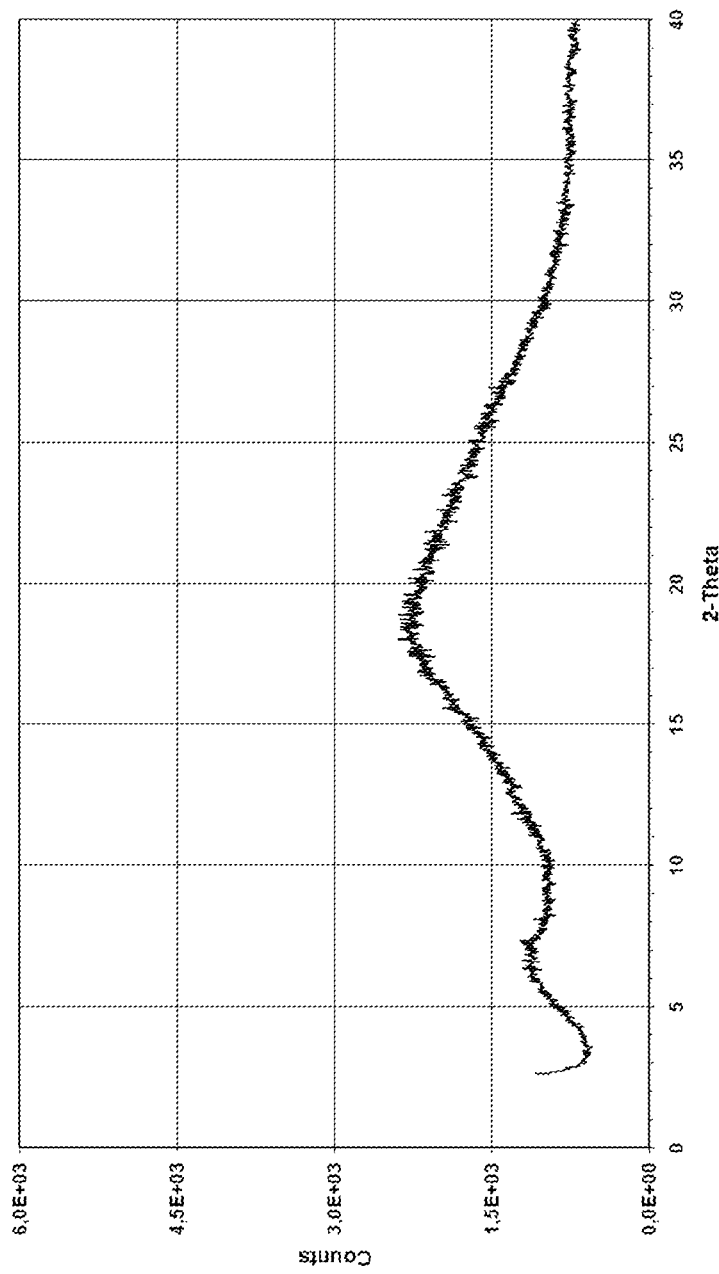
FIG. 8: XRPD pattern of the amorphous form of the compound of formula IV wherein R is hydrogen.

Intermediate IV also exists in an amorphous form, obtainable by dissolving intermediate IV in MeOH at reflux followed by evaporation of the methanol solution until dry. Intermediate IV is obtained in amorphous form having an IR spectrum, DSC pattern and XRPD diffractogram as shown in FIGS. 6, 7 and 8 respectively.

In particular, the amorphous form of intermediate IV presents an IR spectrum having absorption peaks at 2930, 1585, 1557, 1509, 1370, 1224, 1054, 1010, 921, 838 and 650±1.5 cm$^{-1}$.

Said forms of intermediate IV represent a further object of the invention.

Step 4: Treatment of IV with Bases

IV is treated with a sodium hydroxide solution of the solution of IV dissolved in organic solvent to give III.

Sodium hydroxide can be used in a concentration ranging between 0.1M and 2M, preferably between 0.3M and 1M, and more preferably between 0.4M and 0.6M.

Intermediate III is isolated by precipitation by adding an anti-solvent after concentrating the phase consisting of the organic solvent to a small volume.

Figure 9:
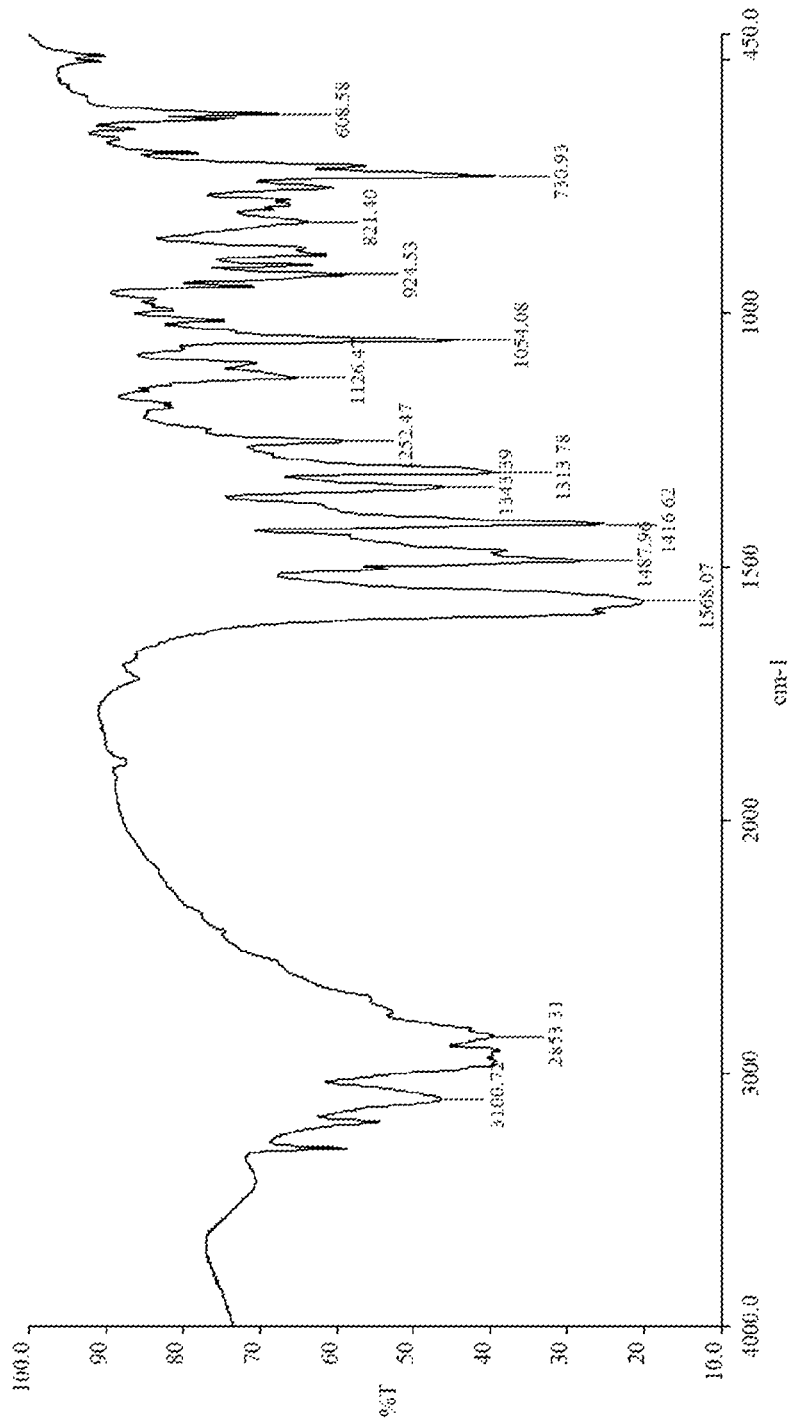
FIG. 9: Infrared spectrum of the crystalline form of the compound of formula III.
Figure 10:
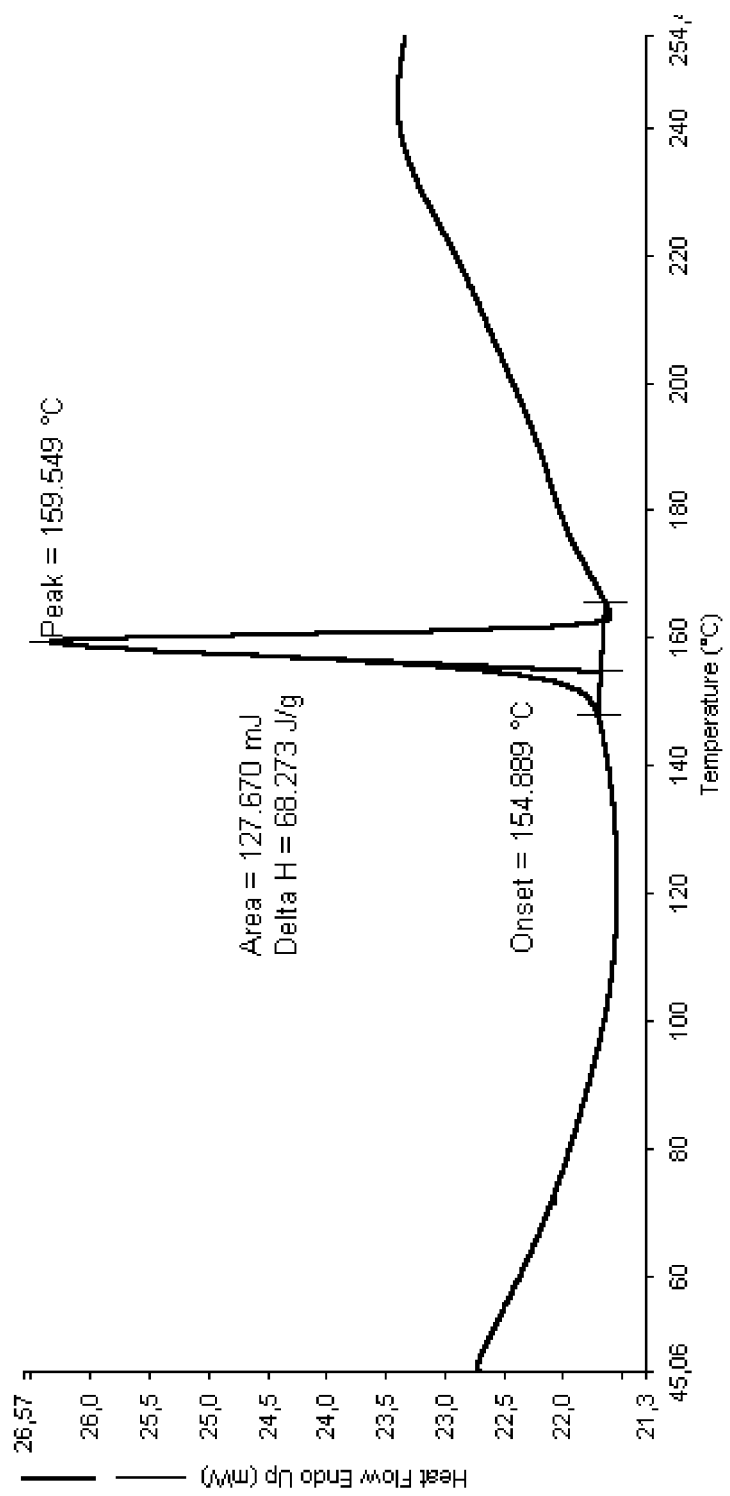
FIG. 10: DSC pattern of the crystalline form of the compound of formula
Figure 11:
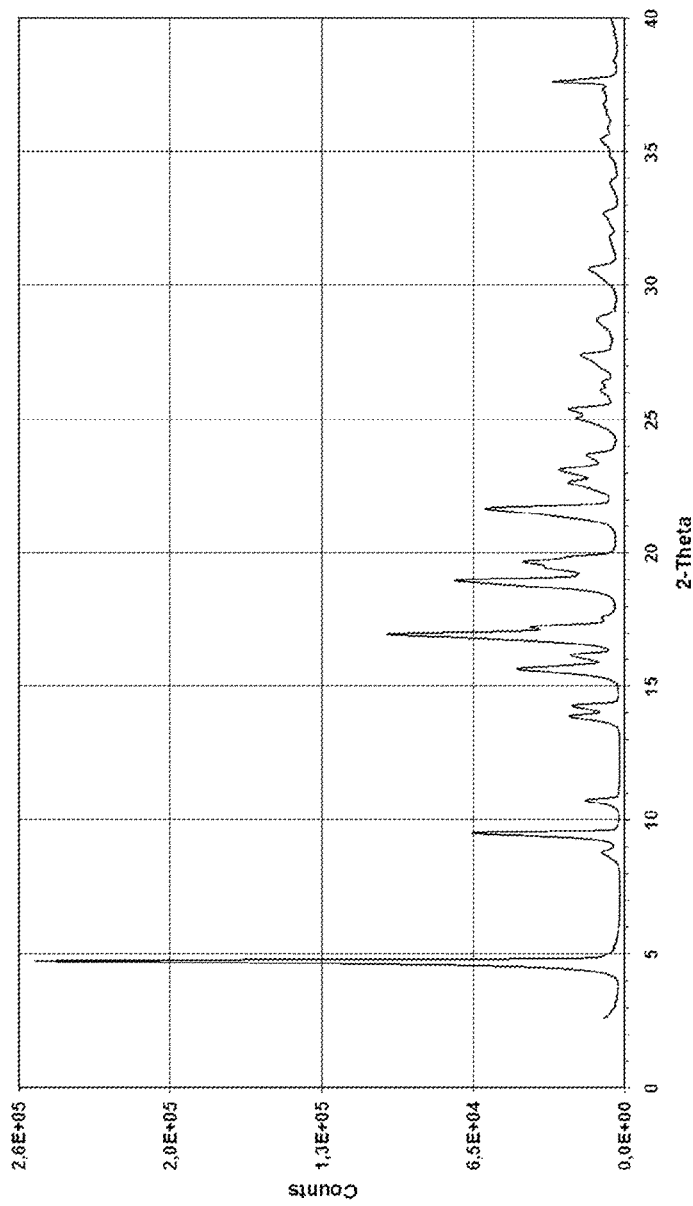
FIG. 11: XRPD pattern of the crystalline form of the compound of formula III.
Figure 12:
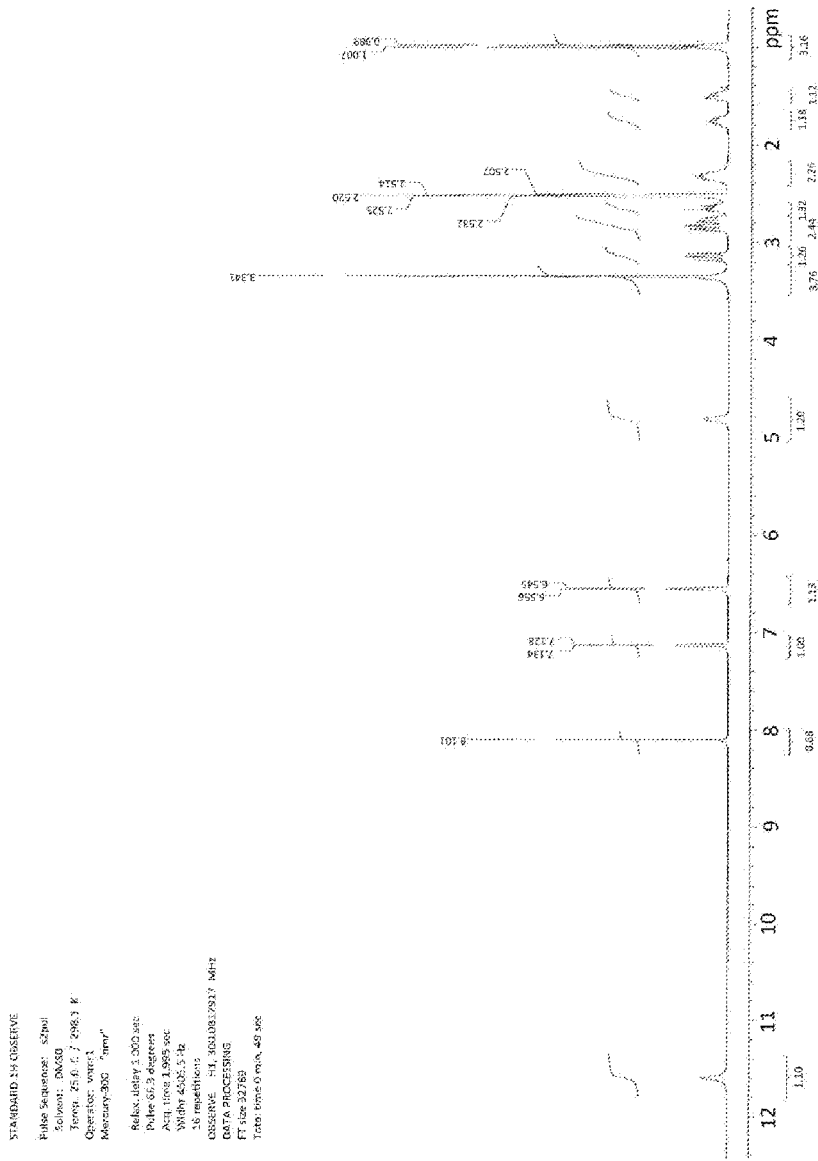
FIG. 12: 1H-NMR spectrum of the crystalline form of the compound of formula III.

Intermediate III exists in a crystalline form obtainable by crystallisation from cyclohexane having an IR spectrum, DSC pattern and XRPD diffractogram as shown in FIGS. 9, 10 and 11 respectively, which represents a further object of the invention.

In particular, said crystalline form of intermediate III presents:
 an IR spectrum comprising characteristic absorption peaks at 3100, 2853, 1568, 1487, 1416, 1343, 1313, 1252, 1126, 1054, 924, 821, 730 and 608±1.5 cm$^{-1}$;
 a DSC pattern comprising an endothermic peak at 159.5° C.;
 an XRPD diffractogram comprising peaks with the following 2θ angle values and intensities: 4.73 (100); 9.49 (25.9); 10.73 (6.9); 15.66 (18.4); 16.94 (40.5); 18.95 (28.9); 21.64 (23.7).

Step 5: N-acylation of III and Consecutive Salification of II

The piperidine nitrogen of the compound of formula III can be derivatised with an acylating agent such as cyanoacetic acid or derivatives thereof.

The N-acylation reaction takes place in the presence of an organic base such as triethylamine, DBU or DIPEA.

The reaction is conducted in polar protic solvent to give the compound of formula II (tofacitinib) in a time ranging between 18 and 72 hours, preferably between 24 and 48 hours.

Compound II can be converted to a pharmaceutically acceptable salt by adding an organic acid such as citric acid to the reaction mixture.

The invention will now be further illustrated by the following examples.

EXAMPLES

The IR spectra were recorded with a Perkin Elmer spectrum 1000 IR instrument. The sample is prepared as a KBr pellet. The spectrum is recorded by performing 16 scans at a resolution of 4 cm$^{-1}$.

The DSC patterns were recorded with a Perkin Elmer Pyris 1 instrument, and 3-5 mg of material were used to prepare the samples. The scans are conducted at the speed of 10° C. a minute.

The NMR spectra were recorded with a Varian Mercury 300 instrument in DMSO at 25° C., 16 scans being performed.

The XRPD spectra were recorded with a Bruker D2 instrument which uses the following parameters: Wavelength CuKα (λ=15419 A)—Energy 30 KV—Step size: 0.02°-2θ Range: 2.6°-40°.

Example 1

81.4 g of VII and 42.92 g of VIII are added to a 21% aqueous solution by weight of $K_2CO_3$.

The mixture is maintained at reflux for 48 h, and 270 ml of methanol is then loaded. The mixture is cooled to room temperature. The mixture is filtered through a Büchner funnel. Intermediate VI (87.5 g) is dissolved at reflux in 2.2 lt of isopropanol, decolourised with activated carbon and recovered after cooling and filtration following partial removal of the solvent by evaporation under vacuum.

Example 2

101 ml of glacial acetic acid is added to a 4:1 mixture of isopropanol/water (925 ml). 185.2 g of intermediate VI is loaded, and the mixture is heated to 50° C. 18.5 g of 5% Pd/C is then loaded, and a hydrogen atmosphere is applied. The mixture is maintained under stirring for 24 h at 50° C. The mixture is filtered through a Büchner funnel. The pH is corrected to a value of 10-12 with 241 g of 30% NaOH solution, and the mixture is then concentrated at low pressure to a residual volume of 420 ml. The mixture is extracted with 500 ml of n-butanol.

The organic phase is concentrated at low pressure to a small volume, and product V is isolated by precipitation with cyclohexane.

Example b 3

Intermediate V (126.7 g) is dissolved in 760 ml of methanol. A solution of 2,3-dibenzoyl-D-tartaric acid monohydrate in methanol (187.5 g in 760 ml) is added by dripping. 20 minutes after the end of pouring, the mixture is seeded with a small amount of compound IV, wherein R is hydrogen.

The mixture is maintained under stirring for 2 h at room temperature, then for 2 h at 10° C. and 1 h at room temperature. The mixture is filtered through a Büchner funnel to obtain 139.9 g of IV, wherein R is hydrogen, with enantiomeric purity exceeding 99%. The product presents an IR spectrum, DSC pattern, XRPD diffractogram and 1H-NMR spectrum as shown in FIGS. 2-5 respectively.

The amorphous form of IV, wherein R is hydrogen, is obtained by dissolving intermediate IV in methanol at reflux and then concentrating the resulting solution to residue; said form presents an IR spectrum, DSC pattern and XRPD diffractogram as shown in FIGS. 6-8 respectively.

Example 4

Intermediate IV, wherein R is hydrogen (128 g), is suspended in n-butanol to which an 0.3N solution of NaOH is added by dripping. The mixture is maintained under stirring for 3 h, after which the phases are separated and the organic phase is washed with 300 ml of water.

The organic phase is concentrated at low pressure to a small volume. Product III (45 g) is obtained by precipitation from cyclohexane. The product presents an IR spectrum, DSC pattern, XRPD diffractogram and 1H-NMR spectrum as shown in FIGS. 9-12 respectively.

Example 5

Intermediate III (44.0 g) is dissolved in n-butanol (132 ml), after which ethyl cyanoacetate (36.8 ml) and DBU (12.9 ml) are added.

The solution is heated to T=50° C. and left under stirring for 24 h.

Citric acid monohydrate (72.7 g), water (66 ml) and n-butanol (176 ml) are added; the mixture is then heated to T =80° C. and maintained under stirring for 1 h, and then under stirring at room temperature for 1 h.

The mixture is further cooled to T=5° C. and maintained under stirring at that temperature for 2 h. The mixture is filtered through a Büchner funnel and finally washed with n-butanol (2×88 mL) and water (44 ml), to give tofacitinib citrate.

The invention claimed is:

1. Process for the preparation of tofacitinib of formula II

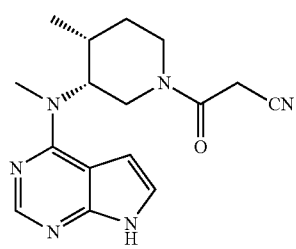

and of a pharmaceutically acceptable salt thereof, comprising the following steps:

a. optically resolving methyl-(4-methylpiperidin-3-yl)-(7H-pirrolo[2,3-d]pyrimidin-4-yl)-amine V

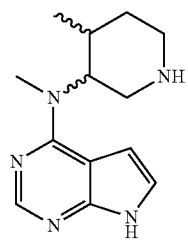

with 2,3-dibenzoyl-D-tartaric acid or with 2,3-di-(p-toluoyl)-D-tartaric acid to give the 2,3-dibenzoyl-D-tartrate or the 2,3-di-(p-toluoyl)-D-tartrate of methyl-((3R,4R)-4-methylpiperidin-3-yl)-(7H-pyrrolo[2,3-d]pyrimidin-4-yl)-amine of formula IV

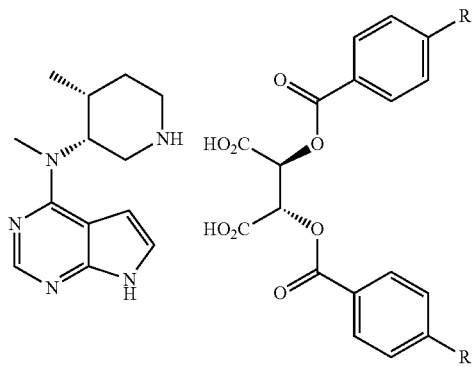

wherein R is hydrogen or methyl;

b. treating IV with bases to give the methyl-((3R,4R)-4-methylpiperidin-3-yl)-(7H-pyrrolo[2,3-d]pyrimidin-4-yl)-amine of formula III

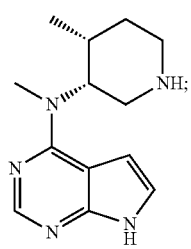

c. converting III into tofacitinib II or a pharmaceutically acceptable salt thereof.

2. The process of claim 1, wherein intermediate IV is obtained with enantiomeric purity greater than 99%.

3. The process of claim 1, comprising the preparation of V by the following steps:

d. condensing 4-chloro-7H-pyrrolo[2,3-d]pyrimidine VII

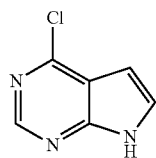

and N,4-dimethyl-1-(phenylmethyl)-3-piperidineamine bishydrochloride VIII

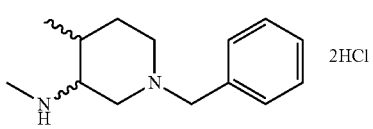

to give methyl-(1-phenylmethyl-4-methylpiperidin-3-yl)-(7H-pyrrolo[2,3-d]pyrimidin-4-yl)-amine VI

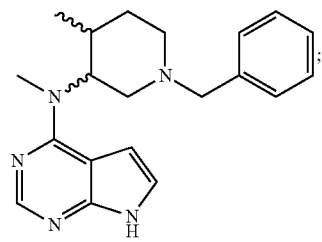

e. hydrogenating VI to give V.

4. The process of claim 1, wherein the converting step of III into tofacitinib II takes place through acylation of III with cyanoacetic acid or a derivative thereof, to give tofacitinib II.

5. The process of claim 1, comprising salifying tofacitinib II to give tofacitinib monocitrate I.

6. Process for the optical resolution of methyl-(4-methylpiperidin-3-yl)-(7H-pyrrolo[2,3-d]pyrimidin-4-yl)-amine V to give methyl-((3R,4R)-4-methylpiperidin-3-yl)-(7H-pyrrolo[2,3-d]pyrimidin-4-yl)-amine III or methyl-((3S,4S)-4-methylpiperidin-3-yl)-(7H-pyrrolo[2,3-d]pyrimidin-4-yl)-amine comprising the following steps:

f. reacting V with 2,3-dibenzoyl-D-tartaric acid or with 2,3-di-(p-toluoyl)-D-tartaric acid to give the 2,3-dibenzoyl-D-tartrate or the 2,3-di-(p-toluoyl)-D-tartrate of methyl((3R,4R)-4-methylpiperidin-3-yl)-(7H-pyrrolo[2,3-d]pyrimidin-4-yl)-amine of formula IV;

g. treating IV with bases to give methyl-((3R,4R)-4-methylpiperidin-3-yl)-(7H-pyrrolo[2,3-d]pyrimidin-4-yl)-amine III; or h. reacting V with 2,3-dibenzoyl-L-tartaric acid or with 2,3-di-(p-toluoyl)-L-tartaric acid to give the 2,3-dibenzoyl-L-tartrate or the 2,3-di-(p-toluoyl)-L-tartrate of methyl-((3S,4S)-4-methylpiperidin-3-yl)-(7H-pyrrolo[2,3-d]pyrimidin-4-yl)-amine;

i. treating the product obtained in step h with bases to give methyl-((3S,4S)-4-methylpiperidin-3-yl)-(7H-pyrrolo[2,3-d]pyrimidin-4-yl)-amine.

7. A compound of formula IV, wherein R is hydrogen or methyl.

8. A crystalline form of the compound of formula IV wherein R is hydrogen, having one or more of the following characteristics:

an IR spectrum comprising absorption peaks at 1723, 1564, 1492, 1414, 1348, 1259, 1177, 1097, 903 and 716±1.5 cm$^{-1}$;

a DSC pattern comprising an endothermic peak at 156.7° C.;

an XPRD diffractogram comprising peaks having the following 2θ angle values and intensities: 7.18 (100); 9.03 (96.4); 9.45 (62.5); 12.35 (61); 15.44 (70.1); 16.57 (58.5); 18.09 (72.6); 20.91 (56.7).

9. An amorphous form of the compound of formula IV wherein R is hydrogen, having an IR spectrum comprising absorption peaks at 2930, 1585, 1557, 1509, 1370, 1224, 1054, 1010, 921, 838 and 650±1.5 cm$^{-1}$.

* * * * *